(12) United States Patent
Ignatyev et al.

(10) Patent No.: US 9,171,650 B2
(45) Date of Patent: Oct. 27, 2015

(54) X-RAY IMAGING

(75) Inventors: Konstantin Ignatyev, Didcot (GB); Alessandro Olivo, London (GB); Peter Munro, Como (AU); Robert Speller, Bedfordshire (GB)

(73) Assignee: UCL BUSINESS PLC, London (GB)

( * ) Notice: Subject to any disclaimer, the term of this patent is extended or adjusted under 35 U.S.C. 154(b) by 150 days.

(21) Appl. No.: 14/233,188

(22) PCT Filed: Jul. 19, 2012

(86) PCT No.: PCT/GB2012/051724
§ 371 (c)(1),
(2), (4) Date: Apr. 24, 2014

(87) PCT Pub. No.: WO2013/011316
PCT Pub. Date: Jan. 24, 2013

(65) Prior Publication Data
US 2014/0233697 A1 Aug. 21, 2014

(30) Foreign Application Priority Data

Jul. 21, 2011 (GB) .................................. 1112537.4

(51) Int. Cl.
*G21K 1/06* (2006.01)
*G01N 23/20* (2006.01)
*A61B 6/00* (2006.01)
*G01N 23/04* (2006.01)

(52) U.S. Cl.
CPC ................ *G21K 1/06* (2013.01); *A61B 6/4233* (2013.01); *A61B 6/484* (2013.01); *A61B 6/585* (2013.01); *G01N 23/04* (2013.01); *G01N 23/20075* (2013.01); *A61B 6/4291* (2013.01); *A61B 6/587* (2013.01); *G01N 2223/313* (2013.01); *G01N 2223/401* (2013.01)

(58) Field of Classification Search
CPC .... A61B 6/4233; A61B 6/4291; A61B 6/484; A61B 6/585; A61B 6/587; A61B 6/4258; G01N 2223/313; G01N 2223/401; G01N 23/04; G01N 23/20075; G21K 1/06; G21K 1/02; G21K 1/025; B29C 33/302; B29C 33/3842; B29C 33/42; B29C 39/34; B29C 39/021; B29C 67/0051; B29C 69/001; B29C 33/301; B29C 33/38; B29C 33/3835; B29C 2083/00
USPC ............................................. 378/36, 62, 204
See application file for complete search history.

(56) References Cited

U.S. PATENT DOCUMENTS 5,684,851 A * 11/1997 Kurbatov et al. ............... 378/87
5,812,629 A * 9/1998 Clauser .......................... 378/62
2007/0183579 A1 8/2007 Baumann et al.
2011/0243300 A1 10/2011 Kaneko et al.

FOREIGN PATENT DOCUMENTS

WO WO 2011/070521 6/2011

* cited by examiner

*Primary Examiner* — Irakli Kiknadze
(74) *Attorney, Agent, or Firm* — Leason Ellis LLP

(57) ABSTRACT

A method of aligning masks for phase imaging or phase contrast imaging in X-ray apparatus using a pixel-type X-ray detector makes use of non-idealities of all real detectors. A mask may be provided before the sample to generate beams, adjacent to the pixels of the detector or both. The method includes moving the mask into a plurality of translational position increments and identifying the increment for which the intensity has a maximum or minimum. The identified value of the increment may vary over the pixels of the detector. Alignment positions are selected in which steps in a plot of the increment over the area of the detector are minimized and/or aligned with the rows and columns of pixels.

14 Claims, 5 Drawing Sheets

US 9,171,650 B2

X-RAY IMAGING

CROSS REFERENCE TO RELATED APPLICATIONS

The present application is a U.S. National Phase of International Patent Application PCT/GB2012/051724, filed Jul. 19, 2012, which claims priority to Great Britain Patent Application No. GB 1112537.4, filed Jul. 21, 2011, each of which is incorporated herein by reference in its entirety.

FIELD OF INVENTION

The invention relates to an apparatus and method for X-ray imaging, in particular phase contrast imaging.

RELATED ART

Conventional X-ray imaging systems are based on absorption of X-rays, and generate an image contrast based on differences in absorption across an image object.

Phase contrast imaging makes use of the variable phase shifts based on the differences in speed of X-rays in an imaged object. Until recently, phase contrast imaging and phase imaging required very high powered X-ray beams such as those produced by synchrotrons which produce high power high quality X-ray beams.

Phase contrast X-ray imaging is described in general terms in a review article by R Lewis, "Medical phase contrast x-ray imaging: current status and future prospects", Phys. Med. Biol. volume 49 (2004) pages 3573 to 3583.

A key point in favour of phase contrast X-ray imaging is that the term responsible for phase changes (the deviation of the real part of the index of refraction from unity) is typically on the order of 1000 times higher than the imaginary part of the index of refraction, which is responsible for the absorption of X-rays in the sample. This means that phase contrast imaging can have dramatically improved sensitivity compared to conventional X-ray imaging methods based on absorption.

A recent proposal, in WO 2008/029107, proposes carrying out phase-contrast imaging using a method that can work with conventional X-ray sources. In this approach, typically a pair of masks are used, one mask in front of the sample to create one or more X-ray beams, and one in front of the detector to block part of the detector pixels. Both masks are geometrically aligned to detector pixels so that the projection of transmission and absorption regions of each mask form a specific pattern on the detector. One of the advantages of the proposed method is that it can deliver short acquisition times.

However, the method proposed in WO 2008/029107 requires accurate alignment of the pair of masks and the X-ray detector which can create difficulties.

SUMMARY OF INVENTION

According to the invention there is provided an apparatus for phase imaging comprising:
a source (2) of X-rays;
a sample stage for mounting a sample;
a sample mask (8) having at least one aperture (32) to define at least one X-ray beam corresponding to the at least one aperture, wherein each X-ray beam has opposed first and second edges;
an X-ray detector having pixels or rows of pixels corresponding to the at least one X-ray beam; and
a detector mask between the sample stage and the X-ray detector having at least one aperture corresponding to the at least one X-ray beam;
further comprising at least one of:
a) a sample mask alignment drive for positioning the sample mask; and
b) a detector mask alignment drive for positioning the detector mask; and
the apparatus further comprising a controller adapted to carry out a method to align at least one of the sample mask and the detector mask.

The invention also provides for a method of aligning at least one mask in an X-ray imaging apparatus in at least one translational and/or rotational direction of the at least one mask, the mask having a plurality of apertures, the method including:
(a) directing X-rays from a source (2) in a z-direction through the mask to the X-ray detector orientated perpendicularly to the X-rays, the X-ray detector having pixels arranged in an x-direction and in a perpendicular y-direction;
(b) for each of a plurality of potential alignment positions in at least one of the translational and/or rotational directions, translating the mask in the x- or y-direction with respect to the X-ray detector to a plurality of translational position increments, identifying for pixels in the detector the translational position increment corresponding to an extremum of the detected intensity profile for that pixel, and hence identifying steps in a predetermined function which separates the regions of the detector that have the same position of the extremum for all pixels in that area;
(c) selecting the alignment position in which the steps in the identified translational position increment over the two-dimensional area of the pixel detector are minimised and/or aligned with the x- and y-directions, and
(d) moving the mask to the selected alignment position.

The invention allows accurate alignment of the masks before measurement using the non-uniformity of the detector pixel response.

BRIEF DESCRIPTION OF DRAWINGS

For the purpose of illustrating the invention, there are depicted in drawings certain embodiments of the invention. However, the invention is not limited to the precise arrangements and instrumentalities of the embodiments depicted in the drawings.

DETAILED DESCRIPTION

Figure 1:
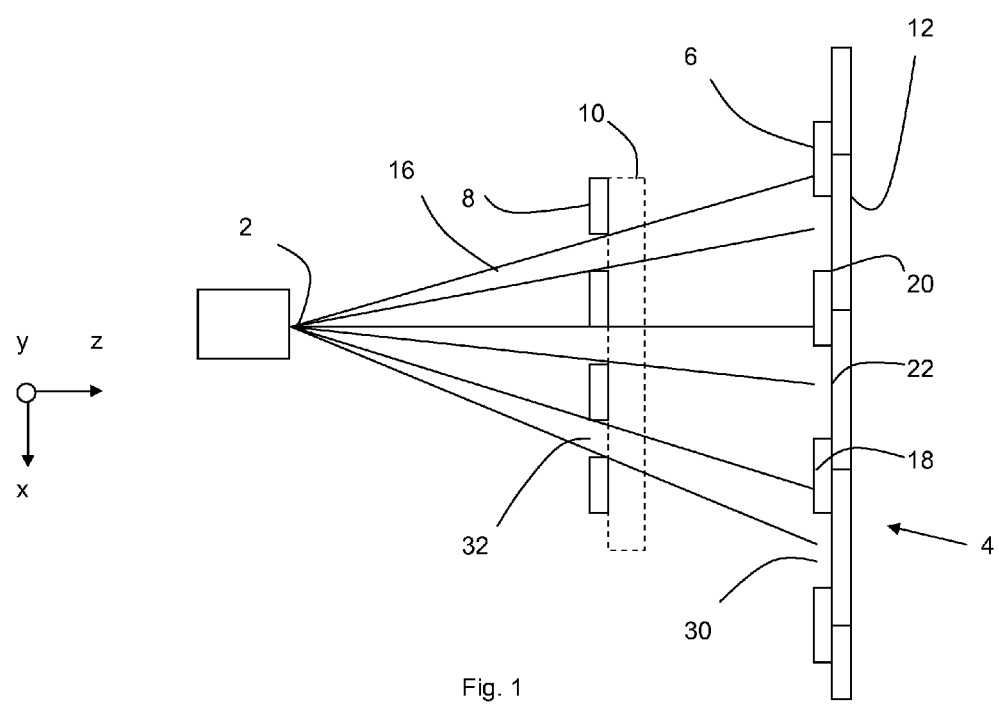
FIG. 1 shows a system according to a first embodiment of the invention.

Referring to FIG. 1, the system according to the first embodiment of the invention consists of an x-ray source 2, an x-ray detector 4, a sample mask 8 placed immediately before the sample region 10 and a detector mask 6. The x-ray source is not a synchrotron source, which could provide collimated and monochromatic X-rays with sufficient flux, instead it is a conventional laboratory-based X-ray source which is commercially available.

For example, the source may be a molybdenum target source; many other commercial sources are available. Such sources are not in general monochromatic, instead although such sources frequently have a dominant energy they in fact emit amounts of energy at other frequencies, and in this sense are polychromatic. Thus, in this specification, "polychromatic" is not intended to require a broad spectrum of frequencies. Further, such commercial sources are also not inherently collimated in the way that synchrotron sources are, instead X-rays are emitted in a range of angles; thus the emitted X-rays are both divergent, polychromatic and uncollimated.

The x-ray detector 4 is made up of a two-dimensional array of pixels 12 in which the pixels extend to form rows and columns (not shown). In the embodiment the detector includes a detector mask 6 defining pixel edges 20.

In order to carry out the phase contrast imaging, the masks 6,8 are aligned to produce a specific shadowing effect in use, as will now be described. In particular, the sample mask has apertures 32 in the form of parallel slits which produce discrete X-ray beams corresponding to rows of pixels in the detector.

The detector mask 6 is arranged to have solid x-ray absorbing regions 18 over the boundaries between discrete pixels 12, defining an edge 20 between the x-ray absorbing regions 18 and apertures or slits 30. Each aperture 30 of the detector mask 6 thus defines the x-ray sensitive region, i.e. the uncovered area 22, of the corresponding pixel 12, since x-rays incident on the detector mask 6 are absorbed.

The detector mask 6, detector pixels 12 and sample mask 8 all need to be aligned so that the X-ray beams created by the apertures 32 in the sample mask are aligned with respective apertures 30 in the detector mask and rows of pixels 12 of the X-ray detector. This requires fine alignment.

This is achieved using three drive units, a sample mask alignment drive for positioning the sample mask, a detector mask alignment drive for positioning the detector mask, and a detector alignment drive for positioning the X-ray detector 4. Each of the drive units is adapted to finely position the respective element.

The apparatus also includes a controller adapted to carry out alignment method, which will now be described in more detail, starting with the mathematical basis.

Both of those masks 6,8 absorb parts of the X-ray beam that do not contribute constructively to the phase contrast, and thus improve the phase contrast signal-to-noise ratio. The sample mask splits the beam into a multitude of individual X-ray beams which are analysed by the detector grating. A typical distance from the source to the detector is about two meters but can be varied within a continuous range.

In the typical setup the gratings are one-dimensional, that is, they consist of a series of transmission slits oriented in one direction, although two-dimensional design is possible as well.

Figure 2:
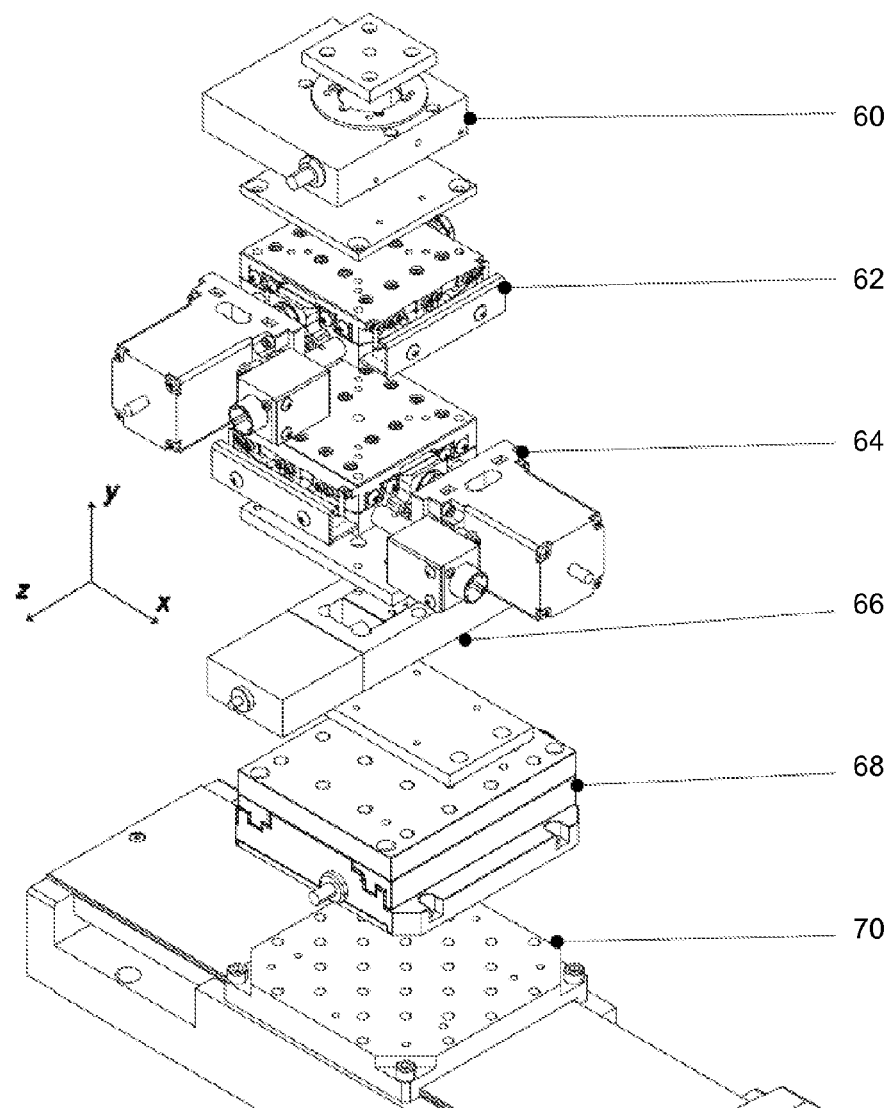
FIG. 2 illustrates a drive unit used in the first embodiment of the invention.

In order for the setup to generate optimal phase contrast images, both gratings as well as the detector have to be aligned to a high precision. This means that all transmission slits of both gratings have to be parallel to each other and to the detector pixel columns in three-dimensional space. For this purpose both gratings are mounted on a drive unit consisting of a serial sequence of six motors (FIG. 2). Thus, each of the drive units consists of six motors.

The lowest motor 70 provides the motion of the gratings in the transverse direction (x-axes shown in FIG. 1). This motion allows varying the proportion of the phase contrast and absorption signal. The next stage 68, provides movement in vertical direction. It is only used to match the vertical position of two gratings and is not used for the actual alignment procedure for a 1D mask. The next stage 66 provides translation in Z-direction which allows changing the projected period of the grating. On top of those stages are three rotation stages 64,62,60 that provide movement about the three orthogonal axes. In all there are six degrees of freedom associated with each grating.

For the alignment of the interferometric systems in both optical and X-ray regimes, various methods based on the analysis of Moire patterns are used. A Moire pattern is generated when two gratings with slightly different period or rotation relative to each other are overlayed.

The inventors therefore first considered the use of Moire patterns but to obtain these patterns the gratings have to be moved far out of the optimal alignment to generate the necessary mismatch in the projected period. This means that it is not a true measure of the system alignment, but rather a measure of a system misalignment in a particular point in space. Efforts were made to calculate the optimal position of the gratings based on the measurement of Moire patterns, but they were not able to provide sufficient accuracy. Also this is not a practical solution in a potential commercial system design with limited space where large translations of gratings are undesirable.

Instead, the inventors realised that the alignment should be performed based on the output of the system itself, in this case based on the X-ray detector signal.

Figure 3:
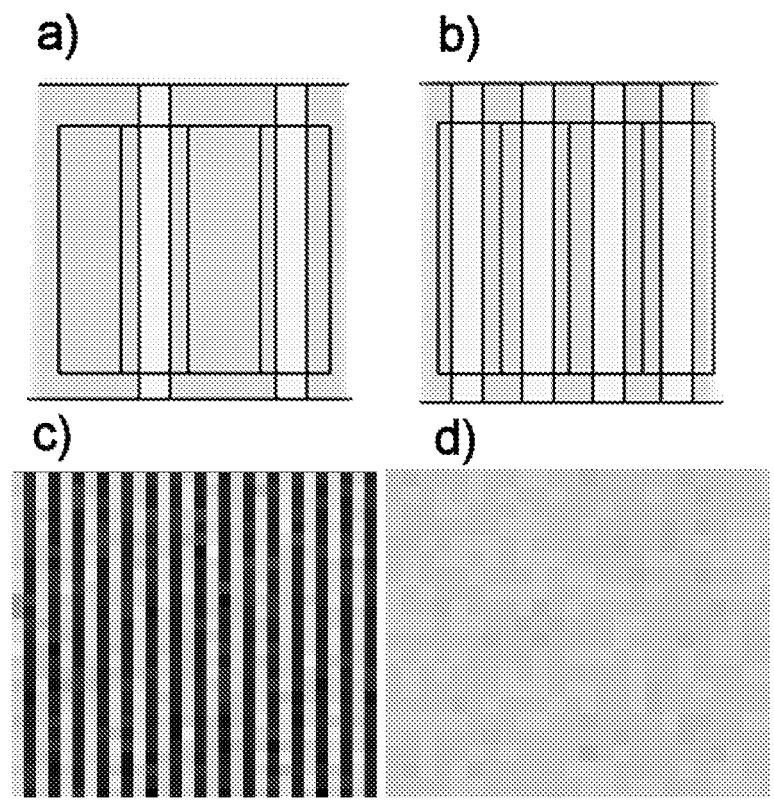
FIG. 3 is a schematic illustrating system alignment.

The complications arising in trying to perform the alignment based on the detector image are shown in FIG. 3. FIG. 3 illustrates two potential mask designs in FIGS. 3a and 3b and the obtained image in respective FIGS. 3c and 3d. One option is a line-skipping mask as shown in FIG. 3a, that is, a mask which blocks every other column of pixels in the detector. This leads to darker lines in the detected image of FIG. 3c which correspond to the blocked pixels which allows easy identification of the columns of pixels that are used. In this case the contrast of the mask image is very good and the alignment can be easily visualised.

However the disadvantage of the line skipping mask is that it blocks more X-rays compared with the alternative, a non-line skipping mask, and that the resolution is reduced. In a non line-skipping mask, shown in FIG. 3b every row of pixels in the X-ray detector corresponds to a slit in the detector mask. In this case, there are no dark lines in the image as shown in FIG. 3d.

The use of the non-line skipping mask brings the significant advantage of reduction in the exposure time and increase in the spatial resolution by a factor of two. Thus, efficient design involves the use of non-line-skipping masks.

Therefore, the inventors realised that the alignment algorithm used needs to work with non-line skipping masks, not just line-skipping masks.

The inventors further realised that there is useful information that can be obtained with an X-ray detector, using the non-uniformity in its response as an analyser tool. The outline of the method and practical steps for applying it to aligning the non-line-skipping mask are presented below.

To first approximation, assuming parallel X-ray beams and 100% efficient and homogenous absorption grating, the intensity of the beam behind the mask can be written as $$I(x,y)=T(x,y)*I_0(x,y) \quad (1)$$

where $I(x,y)$ is the intensity of the beam propagating in z-direction behind the grating, $I_0(x,y)$ is the intensity of the incident beam and $T(x,y)$ is the transmission function representing the grating geometry. The transmission function of the grating shown below can be written as $$T(x, y) = \begin{cases} 1, & \text{if } \sin\left(\frac{2\pi x}{p}\right) \geq L, \\ 0, & \text{otherwise} \end{cases}$$

where P is the period of the grating and L is the parameter that is within the [−1,1] range and is defined by the ratio of the transmission slit width to the grating period P.

The signal recorded by the detector is a modulation of the X-ray beam by the detector point spread function, which describes the efficiency with which the detector converts the incoming X-ray photons into electrical signal as a function of the position of the incoming photon. In case of an ideal detector with uniform and homogenous response function, the signal after the absorption grating would be uniform, with no contrast, due to the fact that the pixel response would not change as a function of the position at which it is illuminated.

However, generally this is never the case. For example, flat panel detectors such as a direct conversion Selenium detector that was used have an active volume consisting of a homogenous layer of semiconductor material and a periodic electrode structure which collects the electrons generated in the active area as a result of X-ray photon interaction with the semiconductor.

Due to manufacturing constraints, the electric field in the active area generated by the electrodes is non-uniform, e.g. decreasing from the center of the pixel defined by the center of the electrode towards the edge of the pixel. As a result, the electron collection efficiency is non-uniform as well. The geometrical detector response then can be described as a periodic function R(x',y') where (x' y') coordinate system lies in the plane of the detector and the x' and y' axis are aligned with pixel borders. Then $$R(x',y')=R(x'+nSx,y'+mSy), \quad (3)$$

where n and m are integers and Sx and Sy is the pixel pitch in the two directions. Here the detector is approximated as a matrix of uniform pixels which is generally not the case, due to individual pixel non-uniformity, however this approximation works well in our case. In common imaging modalities, the effect of the periodicity of the geometrical detector response function is not detectable, due to the fact that the point spread function of the detector masks small deviations on the sub-pixel scale.

However, by using an absorption mask with grating period comparable to the pixel size of the detector, the detector point spread function is effectively sampled, allowing to visualise the detector response at the sub-pixel level. Another way to look at it is that the periodic response of the detector described by equation (3) is modulated with another periodic function of the transmission grating described in (2). The alignment is complete when the periods of the grating function (2) and the detector response function (3) match.

In practical terms this effect can be exploited for the detector aperture alignment. The lateral alignment of the detector mask with the X-ray detector is achieved by translating the detector mask perpendicularly to the direction of the X-rays and to that of the apertures in the mask by small increments until the projection of the center of each transmission slit coincides with the center of each detector pixel column. This condition has to be satisfied for all pixels inside the field of view of the system. This is equivalent to aligning the center of each transmission slit with the vertical pixel edge and then shifting the grating in the horizontal direction by half a pixel. This is a preferable way of aligning the mask since we are more sensitive to pixel edges than to pixel centers.

The detector pixel response function is sampled by scanning the mask in sub-pixel steps in the transverse direction x. The step size determines the resolution of the system alignment and is limited by the precision of the x translation stage. The inventors used apparatus with a precision better than 1 micron, which means that the position of the slit centerline projected onto the detector can be found with one micron accuracy, even though the detector pixel size can be on the order of tens of microns.

Since the sub-pixel detector response variation is a weak effect, to maximise the useful signal the inventors integrate, or average, the signal from neighboring pixels. In a specific embodiment, a moving averaging window of 25×25 pixels was chosen, that is, for each pixel the signal from the surrounding 25×25 pixels was averaged. This results in increased signal-to-noise ratio, and does not affect the alignment resolution, since the alignment resolution is determined by the position increment size. The averaged signal from each pixel is recorded for each step of the scan.

Figure 4:
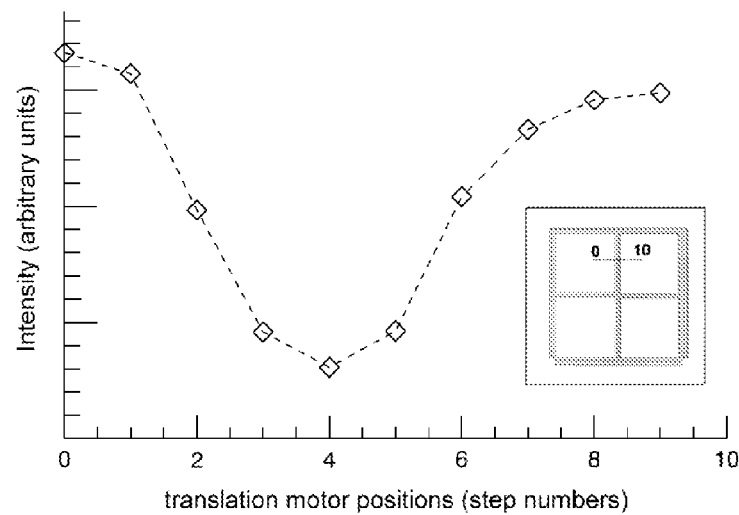
FIG. 4 is a graph of measured recorded intensity as a function of translational increment during alignment.

FIG. 4 illustrates an example of recorded intensity for one of the pixels as a function of translational increments (numbered 1 to 10). The minimum which represents where the mask traverses the pixel edge is clearly visible on the plot. Since, as mentioned earlier, the detector pixel response function is periodic, we only need to scan near the minimum of the function, but because of the uncertainty of the position of the pixel edge, a scan of one period of the function equal to the size of the pixel may be required. In practice, the alignment works well with the scan lengths less than half a pixel.

As a result of the position increment scan, there is a record of the translational increment corresponding to the minimum for of each pixel. We will refer to the numerical index of the translational increment using index i. The numerical index of the minimum of intensity over the X-ray detector array with pixel positions extending in the x and y directions indicated by corresponding indices x and y may be numerically represented by the following function $$G_{x,y}=\arg\min_i\{g_{xy}{}^i\}, \quad (4)$$

which represents the value of i for which there is a minimum over i of the measured X-ray intensity or amplitude g measured for each i, x and y.

Thus, case equation (4) represents a function with the output being the index i of the transitional increment for which the measured intensity has an extremum, here a minimum.

The phase mismatch between the periods of the projection of the transmission grating function in (2) and detector response function in (3) is an indication of the misalignment of the two gratings or the grating and the detector. If $G_{xy}$ is constant then there is no phase mismatch and the alignment condition is satisfied, otherwise motor correction is required.

Figure 6:
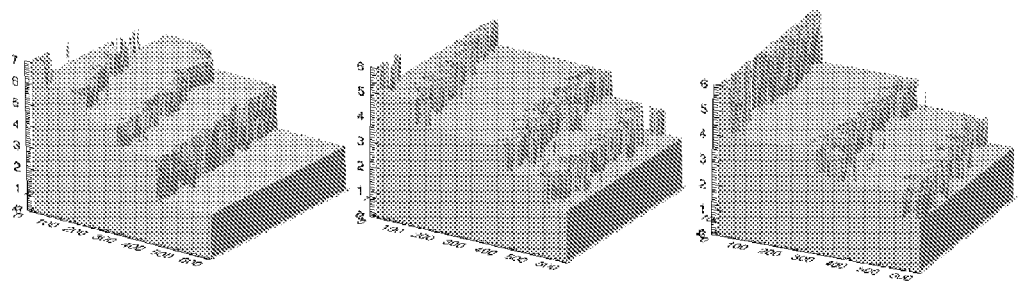
FIG. 6 illustrates values of an alignment function G during the steps of positioning the mask.
Figure 7:
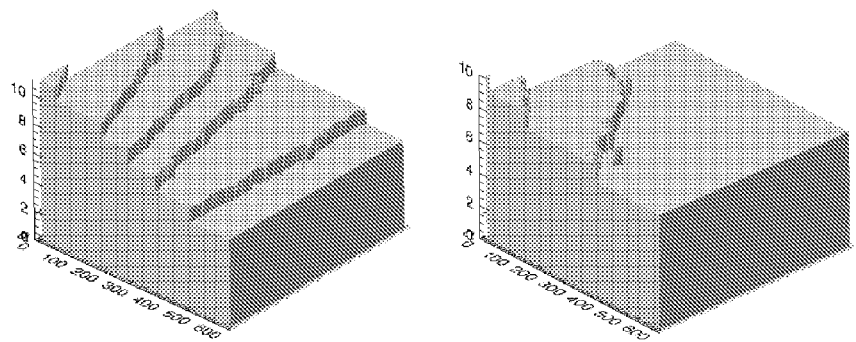
FIG. 7 illustrates values of an alignment function G during the steps of positioning the mask

Example plots of G over the detector are presented in FIGS. 6 and 7. The vertical axis is G and the remaining two axes are the values of x and y over the detector. It will be noted that the values of G have steps which are clearly visible in these plots. The method operates by minimising the number of these steps or aligning the direction and orientation of these steps to align the mask correctly with regard to the detector.

Detector Mask Alignment

Typical steps in which the motor corrections are applied are as follows. First the detector mask is moved into an initial position which satisfies the mask parameter calculations.

Then rotation about x axis (theta scan) is performed for a number of angles and the corresponding step patterns are obtained.

Firstly, the rotation and hence angular positioning of the mask is carried out so that the number of steps in function $G_{xy}$ is equal for both top and bottom areas of the mask. This indicates that both top and bottom of the mask are at the same distance from the detector and that each transmission slit is parallel to the detector plane.

After that the mask is rotated about the z axis which is coincident with the X-ray propagation direction (phi scan). The goal is to orient the steps in function $G_{xy}$ which are visible in the plot of FIG. 6 vertically, which means that now each transmission slit is parallel to the detector pixel column.

FIG. 6 shows patterns for various different angles. The final pattern in FIG. 6 shows the steps aligned perpendicular to the axes—this is the desired alignment at the end of the rotation steps.

In the next step the mask is translated along the Z-direction. With each step along Z, the distance between the steps changes, indicating change in the projected period of the grating function. By moving the Z motor in the correct direction, the period of the steps becomes larger, until they disappear which constitutes optimal alignment condition. Some possible step patterns are shown in FIG. 7. The version with the fewest steps is preferred—it may not be possible to achieve zero steps due to mask non-uniformities.

Then, the mask is aligned in the x- and y-directions by minimising the output as illustrated in FIG. 4.

For finer resolution it is possible to reduce the scanning step size even further and repeat the procedure, however it was found that at some minimal resolution the phase mismatch function $G_{xy}$ is dominated by the random non-uniformities of the mask rather than by systematic misalignment. This suggests that the precision of the method is comfortably greater than required for the XPCi method and, moreover, this method can be used for the characterization of the periodic structures with periods of the order of the detector pixel.

Variations in the method are possible. For example, the detector mask may be omitted and the edges of the pixels of the detector may have the same effect as one of the masks. In this case, it is only necessary to align a single mask with regard to the detector as described previously, i.e. the procedure for aligning the detector mask is followed in order to align this singular mask and the system is considered aligned when the procedure is finished.

As mentioned previously, the transverse motion along x and vertical motion along y do not affect the alignment. The rotation about y axis gives the same effect as translation in z-direction, that is, the change in the projected period, so alignment with the respect to rotation about y-axis can be performed at the same time as z-axis alignment.

Sample Mask Alignment

Figure 5:
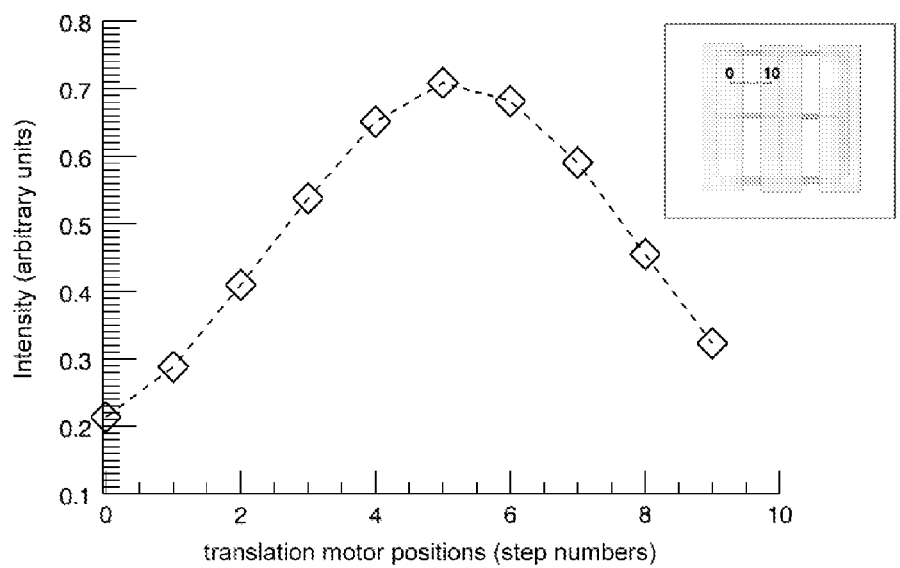
FIG. 5 is a graph of measured recorded intensity as a function of translational increment during alignment.

The procedure for the sample mask alignment is essentially the same as described above. The same principles apply as in the case of the detector mask alignment, but the detector mask now replaces the detector pixel columns, and the sample mask replaces the detector mask. The now aligned detector mask geometrically shapes the detector response, but the idea remains the same: we have to match the projected period of the pre-sample mask with that of the detector mask. The only difference is that if in the case of the detector mask we were looking for the minimum in the pixel response profile, as illustrated in FIG. 4. In contrast, for the case of the sample mask, the required extremum is the maximum when the centreline of the sample transmission slit is aligned with the centreline of the detector transmission slit. Correspondingly, our phase mismatch function now looks like this $$G_{xy} = \arg\max_i \{g_{xy}{}^i\} \quad (5)$$

with typical pixel profile shown in FIG. 5.

Equation (5) represents a function with the output being the index i of the transitional increment for which the measured intensity has an extremum, here a maximum.

Otherwise the phase mismatch function looks similar and alignment steps are exactly as outlined in the section on the detector mask alignment.

Tests have shown the alignment algorithm proposed to be linear and straightforward, so it can be implemented automatically or manually. In automatic mode the alignment of the system is performed with no human intervention.

Where the or each mask has slits, extending for example in the y-direction, there is no need for accurate alignment of the mask in that direction. Instead, there is only a need to align the mask with the pixels in the x-direction perpendicular to the direction in which the slits extend. However, alternative arrangements may use a mask with an array of apertures extending in both the x- and the y-directions and in this case the method includes aligning the mask with respect to translation in both the x- and y directions.

Further, a number of possible processing algorithms are possible. The method of WO2008/029107 is a method of phase contrast imaging, i.e. the method delivers an image that is in fact a linear combination of the phase image (the real part of the refractive index) and the imaginary part. By recording two images and adding them together and subtracting them appropriately, it is also possible to obtain a phase image and an absorption image.

Further details of this are presented in a patent application filed by the same applicant and with number 1112506.9. The method of alignment taught in this application can work just as well with such phase imaging as the phase contrast imaging taught in WO 2008/029107.

The invention claimed is:

1. A method of aligning at least one mask in an X-ray imaging apparatus in at least one translational and/or rotational direction of the at least one mask, the mask having a plurality of apertures, the method including:
   (a) directing X-rays from a source (2) in a z-direction through the mask to the X-ray detector orientated perpendicularly to the X-rays, the X-ray detector having pixels arranged in an x-direction and in a perpendicular y-direction;
   (b) for each of a plurality of potential alignment positions in at least one of the translational and/or rotational directions, translating the mask in the x- or y-direction with respect to the X-ray detector to a plurality of translational position increments, identifying for pixels in the detector the translational position increment corresponding to an extremum of the detected intensity profile for that pixel, and hence identifying steps in a predetermined function which separates the regions of the detector that have the same position of the extremum for all pixels in that area;
   (c) selecting the alignment position in which the steps in the identified translational position increment over the two-dimensional area of the pixel detector are minimised and/or aligned with the x- and y-directions, and
   (d) moving the mask to the selected alignment position.

2. A method according to claim 1, wherein the value of the predetermined function for each potential alignment position is an index value of the translational position increment.

3. A method according to claim 1 of aligning a mask, comprising
- aligning a detector mask with respect to rotations about the x-axis by carrying out the method of claim 1 with:
- the plurality of potential alignment positions being different rotational positions with respect to rotations about the x-axis,
- the identified translational position for each pixel being the translational position with a minimum of the pixel detected intensity, and
- the selected potential alignment position being the potential alignment position in which the number of steps of a map of the identified translational position for each pixel in the x-direction over the two-dimensional area of the pixel detector is most equal at different y-positions of the pixel detector.

4. A method according to claim 1, of aligning a mask, comprising:
- aligning a detector mask with respect to rotations about the z-axis by carrying out the method of claim 1 with:
- the plurality of potential alignment positions being different rotational positions with respect to rotations about the z-axis
- the identified translational position being the translational position in the x-direction with a minimum of the detected intensity for each pixel, and
- the selected potential alignment position being the potential alignment position in which the steps of a map of the identified translational position for each pixel over the two-dimensional area of the pixel detector extend in the y-direction.

5. A method according to claim 1 of aligning a mask, the method including:
- aligning a detector mask with respect to displacement along the z-axis by carrying out the method of claim 1 with:
- the plurality of potential alignment positions being different translational positions with respect to movement along the z-axis,
- the identified translational position for each pixel being a translational position in the x-direction with the minimum of the detected intensity, and
- the selected potential alignment position being the potential alignment position in which the number of steps of a map of the identified translational position for each pixel over the two-dimensional area of the pixel detector extend is minimised.

6. A method according to claim 1 of aligning a mask, the method including:
- aligning a sample mask with respect to rotations about the x-axis by carrying out the method of claim 1 with:
- the plurality of potential alignment positions being different rotational positions of the sample mask with respect to rotations about the x-axis,
- the identified translational position for each pixel being the translational position in the x-direction with a maximum of the detected intensity, and
- the selected potential alignment position being the potential alignment position in which the number of steps of a map of the identified translational position for each pixel in the x-direction over the two-dimensional area of the pixel detector is most equal at different y-positions of the pixel detector.

7. A method according to claim 1 of aligning a mask, the method including:
- aligning the sample mask with respect to rotations about the z-axis by carrying out the method of claim 1 with:
- the plurality of potential alignment positions for each pixel being different rotational positions of the sample mask with respect to rotations about the z-axis,
- the identified translational position being the translational position in the x-direction with a minimum of the detected intensity, and
- the selected potential alignment position being the potential alignment position in which the steps of a map of the identified translational position for each pixel over the two-dimensional area of the pixel detector extend in the y-direction.

8. A method according to claim 1 of aligning a mask, the method including:
- aligning the sample mask with respect to displacement along the z-axis by carrying out the method of claim 1 with:
- the plurality of potential alignment positions being different translational positions of the sample mask with respect to movement along the z-axis,
- the identified translational position for each pixel being a translational position in the x-direction with the maximum of the detected intensity, and
- the selected potential alignment position being the potential alignment position in which the number of steps of a map of the identified translational position for each pixel over the two-dimensional area of the pixel detector extend is minimised.

9. A method according to claim 1 of aligning a sample mask and a detector mask in phase contrast or phase imaging apparatus, the method comprising:
- introducing the detector mask in front of the X-ray detector;
- aligning the detector mask to align the detector mask with respect to rotations about the x-axis, rotations about the z-axis and translation about the z-axis by performing the following steps:
  - aligning a detector mask with respect to displacement along the z-axis by carrying out the method of claim 1 with:
  - the plurality of potential alignment positions being different translational positions with respect to movement along the z-axis,
  - the identified translational position for each pixel being a translational position in the x-direction with the minimum of the detected intensity, and
  - the selected potential alignment position being the potential alignment position in which the number of steps of a map of the identified translational position for each pixel over the two-dimensional area of the pixel detector extend is minimised,
  - the plurality of potential alignment positions being different rotational positions with respect to rotations about the z-axis
  - the identified translational position being the translational position in the x-direction with a minimum of the detected intensity for each pixel, and
  - the selected potential alignment position being the potential alignment position in which the steps of a map of the identified translational position for each pixel over the two-dimensional area of the pixel detector extend in the y-direction;
  - aligning a detector mask with respect to rotations about the x-axis by carrying out the method of claim 1 with:
  - the plurality of potential alignment positions being different rotational positions with respect to rotations about the x-axis, the identified translational position for each pixel being the translational position with a minimum of the pixel detected intensity, and the selected potential alignment position being the potential alignment position in which the number of steps of a map of the identified translational position for each pixel in the x-direction over the two-dimensional area of the pixel detector is most equal at different y-positions of the pixel detector;

introducing the sample mask in front of the detector mask, and aligning the sample mask to align the sample mask with respect to rotations about the x-axis, rotations about the z-axis and translation about the z-axis by performing the following steps:

aligning the sample mask with respect to rotations about the z-axis by carrying out the method of claim 1 with:

the plurality of potential alignment positions for each pixel being different rotational positions of the sample mask with respect to rotations about the z-axis, the identified translational position being the translational position in the x-direction with a minimum of the detected intensity, and the selected potential alignment position being the potential alignment position in which the steps of a map of the identified translational position for each pixel over the two-dimensional area of the pixel detector extend in the y-direction;

aligning the sample mask with respect to rotations about the z-axis by carrying out the method of claim 1 with:

the plurality of potential alignment positions for each pixel being different rotational positions of the sample mask with respect to rotations about the z-axis, the identified translational position being the translational position in the x-direction with a minimum of the detected intensity, and the selected potential alignment position being the potential alignment position in which the steps of a map of the identified translational position for each pixel over the two-dimensional area of the pixel detector extend in the y-direction; and aligning the sample mask with respect to displacement along the z-axis by carrying out the method of claim 1 with:

the plurality of potential alignment positions being different translational positions of the sample mask with respect to movement along the z-axis, the identified translational position for each pixel being a translational position in the x-direction with the maximum of the detected intensity, and the selected potential alignment position being the potential alignment position in which the number of steps of a map of the identified translational position for each pixel over the two-dimensional area of the pixel detector extend is minimised.

10. A method according to claim 1 wherein at least one mask includes rows of apertures in the x-direction and in the y-direction, the method including aligning the at least one mask with respect to translation along both the x- and y-axis.

11. An apparatus for phase contrast imaging, comprising:
a source (2) of X-rays;
a sample stage for mounting a sample;
a sample mask (8) having at least one aperture (32) to define at least one X-ray beam corresponding to the at least one aperture, wherein each X-ray beam has opposed first and second edges;
an X-ray detector having pixels or rows of pixels corresponding to the at least one X-ray beam; and
a detector mask between the sample stage and the X-ray detector having at least one aperture corresponding to the at least one X-ray beam;
further comprising at least one of:
a) a sample mask alignment drive for positioning the sample mask; and
b) a detector mask alignment drive for positioning the detector mask; and
the apparatus further comprising a controller adapted to carry out the method of claim 1 to align at least one of the sample mask and the detector mask.

12. An apparatus according to claim 11 comprising both a) the sample mask alignment drive and b) the detector mask alignment drive.

13. An apparatus according to claim 12 wherein the sample mask alignment drive has a plurality of stages to position the sample mask in three rotational axes and three translational directions.

14. An apparatus according to claim 12 wherein the detector mask alignment drive has a plurality of stages to position the detector mask in three rotational axes and three translational directions.

* * * * *